(12) United States Patent
Hart

(10) Patent No.: US 9,877,775 B2
(45) Date of Patent: Jan. 30, 2018

(54) ELECTROSURGICAL INSTRUMENT WITH A KNIFE BLADE STOP

(71) Applicant: COVIDIEN LP, Mansfield, MA (US)

(72) Inventor: Keir Hart, Lafayette, CO (US)

(73) Assignee: COVIDIEN LP, Mansfield, MA (US)

( * ) Notice: Subject to any disclaimer, the term of this patent is extended or adjusted under 35 U.S.C. 154(b) by 325 days.

(21) Appl. No.: 14/152,690

(22) Filed: Jan. 10, 2014

(65) Prior Publication Data

US 2014/0276803 A1 Sep. 18, 2014

Related U.S. Application Data

(60) Provisional application No. 61/778,057, filed on Mar. 12, 2013.

(51) Int. Cl.
*A61B 18/14* (2006.01)
*A61B 17/295* (2006.01)
(Continued)

(52) U.S. Cl.
CPC ........ *A61B 18/1445* (2013.01); *A61B 17/285* (2013.01); *A61B 17/295* (2013.01); *A61B 2017/2926* (2013.01); *A61B 2017/2936* (2013.01); *A61B 2018/1455* (2013.01); *A61B 2090/034* (2016.02)

(58) Field of Classification Search
CPC ................ A61B 17/285; A61B 17/295; A61B 2018/1452; A61B 2018/1455
See application file for complete search history.

(56) References Cited

U.S. PATENT DOCUMENTS

D249,549 S 9/1978 Pike
D263,020 S 2/1982 Rau, III
(Continued)

FOREIGN PATENT DOCUMENTS

CN 201299462 9/2009
DE 2415263 10/1975
(Continued)

OTHER PUBLICATIONS

U.S. Appl. No. 08/926,869, filed Sep. 10, 1997, James G. Chandler.
(Continued)

*Primary Examiner* — Ronald Hupczey, Jr.

(57) ABSTRACT

An electrosurgical forceps is provided with a shaft that extends from a housing of the electrosurgical forceps. An end effector assembly operably coupled to a distal end of the shaft includes a pair of first and second jaw members having proximal and distal ends. One or both of the first and second jaw members is movable from an open configuration for positioning tissue therebetween, to a clamping configuration for grasping tissue therebetween. A knife blade assembly includes a knife blade that is translatable within the first and second jaw members when the first and second jaw members are in the clamping configuration. The knife blade assembly includes a knife blade stop configured to contact at least a portion of the proximal end of the second jaw member when the first and second jaw members are in the open configuration to limit translation of the knife blade assembly.

15 Claims, 8 Drawing Sheets

(51) Int. Cl.
    *A61B 17/29*     (2006.01)
    *A61B 17/285*     (2006.01)
    *A61B 90/00*     (2016.01)

(56) References Cited

U.S. PATENT DOCUMENTS

| | | |
|---|---|---|
| D295,893 S | 5/1988 | Sharkany et al. |
| D295,894 S | 5/1988 | Sharkany et al. |
| D298,353 S | 11/1988 | Manno |
| D299,413 S | 1/1989 | Decarolis |
| D343,453 S | 1/1994 | Noda |
| D348,930 S | 7/1994 | Olson |
| D349,341 S | 8/1994 | Lichtman et al. |
| D354,564 S | 1/1995 | Medema |
| D358,887 S | 5/1995 | Feinberg |
| 5,445,638 A | 8/1995 | Rydell et al. |
| 5,456,684 A | 10/1995 | Schmidt et al. |
| 5,458,598 A | 10/1995 | Feinberg et al. |
| 5,599,351 A | 2/1997 | Haber et al. |
| D384,413 S | 9/1997 | Zlock et al. |
| H1745 H | 4/1998 | Paraschac |
| 5,800,449 A | 9/1998 | Wales |
| 5,826,776 A | 10/1998 | Schulze et al. |
| 5,827,279 A | 10/1998 | Hughett et al. |
| D402,028 S | 12/1998 | Grimm et al. |
| D408,018 S | 4/1999 | McNaughton |
| 5,938,027 A | 8/1999 | Soroff et al. |
| D416,089 S | 11/1999 | Barton et al. |
| D424,694 S | 5/2000 | Tetzlaff et al. |
| D425,201 S | 5/2000 | Tetzlaff et al. |
| D617,900 S | 6/2000 | Kingsley et al. |
| H1904 H | 10/2000 | Yates et al. |
| 6,216,868 B1 | 4/2001 | Rastegar et al. |
| D449,886 S | 10/2001 | Tetzlaff et al. |
| D453,923 S | 2/2002 | Olson |
| D454,951 S | 3/2002 | Bon |
| D457,958 S | 5/2002 | Dycus et al. |
| D457,959 S | 5/2002 | Tetzlaff et al. |
| H2037 H | 7/2002 | Yates et al. |
| 6,443,970 B1 | 9/2002 | Schulze et al. |
| D465,281 S | 11/2002 | Lang |
| D466,209 S | 11/2002 | Bon |
| D493,888 S | 8/2004 | Reschke |
| D496,997 S | 10/2004 | Dycus et al. |
| D499,181 S | 11/2004 | Dycus et al. |
| D502,994 S | 3/2005 | Blake, III |
| D509,297 S | 9/2005 | Wells |
| D525,361 S | 7/2006 | Hushka |
| 7,101,371 B2 | 9/2006 | Dycus et al. |
| D531,311 S | 10/2006 | Guerra et al. |
| D533,274 S | 12/2006 | Visconti et al. |
| D533,942 S | 12/2006 | Kerr et al. |
| 7,150,749 B2* | 12/2006 | Dycus ............... A61B 18/1445 606/32 |
| D535,027 S | 1/2007 | James et al. |
| D538,932 S | 3/2007 | Malik |
| D541,418 S | 4/2007 | Schechter et al. |
| D541,611 S | 5/2007 | Aglassinger |
| D541,938 S | 5/2007 | Kerr et al. |
| D545,432 S | 6/2007 | Watanabe |
| D547,154 S | 7/2007 | Lee |
| D564,662 S | 3/2008 | Moses et al. |
| D567,943 S | 4/2008 | Moses et al. |
| D575,395 S | 8/2008 | Hushka |
| D575,401 S | 8/2008 | Hixson et al. |
| D582,038 S | 12/2008 | Swoyer et al. |
| 7,597,693 B2* | 10/2009 | Garrison ............ A61B 18/1445 606/46 |
| D617,901 S | 6/2010 | Unger et al. |
| D617,902 S | 6/2010 | Twomey et al. |
| D617,903 S | 6/2010 | Unger et al. |
| D618,798 S | 6/2010 | Olson et al. |
| D621,503 S | 8/2010 | Otten et al. |
| D627,462 S | 11/2010 | Kingsley |
| D628,289 S | 11/2010 | Romero |
| D628,290 S | 11/2010 | Romero |
| D630,324 S | 1/2011 | Reschke |
| D649,249 S | 11/2011 | Guerra |
| D649,643 S | 11/2011 | Allen, IV et al. |
| D661,394 S | 6/2012 | Romero et al. |
| 8,679,140 B2 | 3/2014 | Butcher |
| RE44,834 E | 4/2014 | Dumbauld |
| 8,968,313 B2* | 3/2015 | Larson ............... A61B 18/1447 606/51 |
| 2010/0023009 A1* | 1/2010 | Moses ............... A61B 17/2812 606/51 |
| 2013/0138102 A1* | 5/2013 | Twomey ........... A61B 18/1445 606/45 |
| 2014/0031821 A1 | 1/2014 | Garrison |
| 2014/0031860 A1 | 1/2014 | Stoddard et al. |
| 2014/0046323 A1 | 2/2014 | Payne et al. |
| 2014/0052128 A1 | 2/2014 | Townsend et al. |
| 2014/0066910 A1 | 3/2014 | Nau, Jr. |
| 2014/0066911 A1 | 3/2014 | Nau, Jr. |
| 2014/0074091 A1 | 3/2014 | Arya et al. |

FOREIGN PATENT DOCUMENTS

| | | |
|---|---|---|
| DE | 2514501 | 10/1976 |
| DE | 2627679 | 1/1977 |
| DE | 3423356 | 6/1986 |
| DE | 3612646 | 4/1987 |
| DE | 3627221 | 2/1988 |
| DE | 8712328 | 3/1988 |
| DE | 4303882 | 8/1994 |
| DE | 4403252 | 8/1995 |
| DE | 19515914 | 7/1996 |
| DE | 19506363 | 8/1996 |
| DE | 29616210 | 1/1997 |
| DE | 19608716 | 4/1997 |
| DE | 19751106 | 5/1998 |
| DE | 19751108 | 5/1999 |
| DE | 10031773 | 11/2001 |
| DE | 19946527 | 12/2001 |
| DE | 20121161 | 4/2002 |
| DE | 10045375 | 10/2002 |
| DE | 10 2004 026179 | 12/2005 |
| DE | 20 2007 009318 | 8/2007 |
| DE | 20 2007 009165 | 10/2007 |
| DE | 20 2007 009317 | 10/2007 |
| DE | 20 2007 016233 | 3/2008 |
| DE | 19738457 | 1/2009 |
| DE | 10 2008 018406 | 7/2009 |
| EP | 1159926 | 12/2001 |
| EP | 1281878 | 10/2005 |
| EP | 2294998 | 3/2011 |
| EP | 2347725 | 7/2011 |
| JP | 61-501068 | 9/1984 |
| JP | 6-502328 | 3/1992 |
| JP | 5-5106 | 1/1993 |
| JP | 5-40112 | 2/1993 |
| JP | 6-030945 | 2/1994 |
| JP | 6-121797 | 5/1994 |
| JP | 6-285078 | 10/1994 |
| JP | 6-343644 | 12/1994 |
| JP | 6-511401 | 12/1994 |
| JP | 7-265328 | 10/1995 |
| JP | 8-56955 | 3/1996 |
| JP | 8-317936 | 3/1996 |
| JP | 8-289895 | 5/1996 |
| JP | 8-252263 | 10/1996 |
| JP | 8-317934 | 12/1996 |
| JP | 9-000538 | 1/1997 |
| JP | 9-10223 | 1/1997 |
| JP | 9-122138 | 5/1997 |
| JP | 10-000195 | 1/1998 |
| JP | 10-24051 | 1/1998 |
| JP | 11-070124 | 5/1998 |
| JP | 10-155798 | 6/1998 |
| JP | 2000-102545 | 9/1998 |
| JP | 11-47149 | 2/1999 |
| JP | 11-47150 | 2/1999 |
| JP | 11-169381 | 6/1999 |
| JP | 11-192238 | 7/1999 |

(56) References Cited

FOREIGN PATENT DOCUMENTS

| JP | 11-244298 | 9/1999 |
|---|---|---|
| JP | 2000-135222 | 5/2000 |
| JP | 2000-342599 | 12/2000 |
| JP | 2000-350732 | 12/2000 |
| JP | 2001-8944 | 1/2001 |
| JP | 2001-29355 | 2/2001 |
| JP | 2001-29356 | 2/2001 |
| JP | 2001-128990 | 5/2001 |
| JP | 2001-190564 | 7/2001 |
| JP | 2001-3400 | 11/2001 |
| JP | 2002-528166 | 3/2002 |
| JP | 2002-136525 | 5/2002 |
| JP | 2003-116871 | 4/2003 |
| JP | 2003-175052 | 6/2003 |
| JP | 2003-245285 | 9/2003 |
| JP | 2004-517668 | 6/2004 |
| JP | 2004-528869 | 9/2004 |
| JP | 2005-152663 | 6/2005 |
| JP | 2005-253789 | 9/2005 |
| JP | 2005-312807 | 10/2005 |
| JP | 2006-015078 | 1/2006 |
| JP | 2006-501939 | 1/2006 |
| JP | 2006-095316 | 4/2006 |
| JP | 2011-125195 | 6/2011 |
| SU | 401367 | 11/1974 |
| WO | WO 00/36986 | 6/2000 |
| WO | WO 00/59392 | 10/2000 |
| WO | WO 01/15614 | 3/2001 |
| WO | WO 01/54604 | 8/2001 |
| WO | WO 02/045589 | 6/2002 |
| WO | WO 05/110264 | 11/2005 |
| WO | WO 06/021269 | 3/2006 |
| WO | WO 08/040483 | 4/2008 |
| WO | WO 2011/018154 | 2/2011 |

OTHER PUBLICATIONS

U.S. Appl. No. 09/177,950, filed Oct. 23, 1998, Randel A. Frazier.
U.S. Appl. No. 09/387,883, filed Sep. 1, 1999, Dale F. Schmaltz.
U.S. Appl. No. 09/591,328, filed Jun. 9, 2000, Thomas P. Ryan.
U.S. Appl. No. 12/336,970, filed Dec. 17, 2008, Paul R. Sremeich.
U.S. Appl. No. 13/731,674, filed Dec. 31, 2012, Siebrecht.
U.S. Appl. No. 14/019,031, filed Sep. 5, 2013, Garrison.
U.S. Appl. No. 14/019,094, filed Sep. 5, 2013, Garrison.
U.S. Appl. No. 14/032,486, filed Sep. 20, 2013, Kendrick.
U.S. Appl. No. 14/035,423, filed Sep. 24, 2013, Garrison.
U.S. Appl. No. 14/037,772, filed Sep. 26, 2013, Frushour.
U.S. Appl. No. 14/041,995, filed Sep. 30, 2013, Kendrick.
U.S. Appl. No. 14/042,947, filed Oct. 1, 2013, Craig.
U.S. Appl. No. 14/043,039, filed Oct. 1, 2013, Rusin.
U.S. Appl. No. 14/043,322, filed Oct. 1, 2013, O'Neill.
U.S. Appl. No. 14/047,474, filed Oct. 7, 2013, Mueller.
U.S. Appl. No. 14/050,593, filed Oct. 10, 2013, Plaven.
U.S. Appl. No. 14/052,827, filed Oct. 14, 2013, Nau.
U.S. Appl. No. 14/052,856, filed Oct. 14, 2013, Latimer.
U.S. Appl. No. 14/052,871, filed Oct. 14, 2013, Kappus.
U.S. Appl. No. 14/054,173, filed Oct. 15, 2013, Payne.
U.S. Appl. No. 14/054,573, filed Oct. 15, 2013, Harper.
U.S. Appl. No. 14/064,310, filed Oct. 28, 2013, Reschke.
U.S. Appl. No. 14/065,644, filed Oct. 29, 2013, Reschke.
U.S. Appl. No. 14/080,564, filed Nov. 14, 2013, Lawes.
U.S. Appl. No. 14/080,581, filed Nov. 14, 2013, Kerr.
U.S. Appl. No. 14/083,696, filed Nov. 19, 2013, Horner.
U.S. Appl. No. 14/086,399, filed Nov. 21, 2013, Allen.
U.S. Appl. No. 14/091,505, filed Nov. 27, 2013, Garrison.
U.S. Appl. No. 14/091,521, filed Nov. 27, 2013, Garrison.
U.S. Appl. No. 14/091,532, filed Nov. 27, 2013, Garrison.
U.S. Appl. No. 14/098,953, filed Dec. 6, 2013, Cunningham.
U.S. Appl. No. 14/100,237, filed Dec. 9, 2013, Reschke.
U.S. Appl. No. 14/103,971, filed Dec. 12, 2013, Roy.
U.S. Appl. No. 14/105,374, filed Dec. 13, 2013, Moua.
U.S. Appl. No. 14/109,459, filed Dec. 17, 2013, Hoarau.
U.S. Appl. No. 14/149,343, filed Jan. 7, 2014, Schmaltz.
U.S. Appl. No. 14/152,618, filed Jan. 10, 2014, Artale.
U.S. Appl. No. 14/152,690, filed Jan. 10, 2014, Hart.
U.S. Appl. No. 14/153,346, filed Jan. 13, 2014, Collings.
U.S. Appl. No. 14/162,192, filed Jan. 23, 2014, Garrison.
U.S. Appl. No. 14/164,569, filed Jan. 27, 2014, Heard.
U.S. Appl. No. 14/169,358, filed Jan. 31, 2014, Reschke.
U.S. Appl. No. 14/172,050, filed Feb. 4, 2014, Johnson.
U.S. Appl. No. 14/173,391, filed Feb. 5, 2014, Kharin.
U.S. Appl. No. 14/176,341, filed Feb. 10, 2014, Hart.
U.S. Appl. No. 14/176,684, filed Feb. 10, 2014, Chojin.
U.S. Appl. No. 14/177,812, filed Feb. 11, 2014, Dycus.
U.S. Appl. No. 14/178,540, filed Feb. 12, 2014, Anderson.
U.S. Appl. No. 14/182,894, filed Feb. 18, 2014, Hart.
U.S. Appl. No. 14/182,967, filed Feb. 18, 2014, Latimer.
U.S. Appl. No. 14/183,090, filed Feb. 18, 2014, Arts.
U.S. Appl. No. 14/188,935, filed Feb. 25, 2014, Reschke.
U.S. Appl. No. 14/196,066, filed Mar. 4, 2014, McCullough.
U.S. Appl. No. 14/204,770, filed Mar. 11, 2014, Dumbauld.
Michael Choti, "Abdominoperineal Resection with the LigaSure Vessel Sealing System and LigaSure Atlas 20 cm Open Instrument" ; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps" , Feb. 6, 1967 (Feb. 2, 1965), British Medical Journal Feb. 6, 1976, vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales-Product Literature; Dec. 31, 2000.
Johnson et al. "Evaluation of a Bipolar Electrothermal Vessel Sealing Device in Hemorrhoidectomy" Sales-Product Literature; Jan. 2004.
E. David Crawford "Evaluation of a New Vessel Sealing Device in Urologic Cancer Surgery" Sales-Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Burdette et al. "In Vivo Probe Measurement Technique for Determining Dielectric Properties At VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing SyStem: Revolutionary Hemostasis Product for General Surgery"; Sales-Product Literature 1999.
LigaSure Vessel Sealing System, the Seal of Confidence in General, Gynecologic, Urologic, and Laparaoscopic Surgery; Sales-Product Literature; Apr. 2002.

(56) References Cited

OTHER PUBLICATIONS

Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales-Product Literature 2001.
Bergdahl et al. "Studies on Coagulation and the Development of an Automatic Computerized Bipolar Coagulator" J.Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales-Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul.-Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'L Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales-Product Literature 2000.
Jarrett et al., "Use of the LigaSure Vessel Sealing System for Peri-Hilar Vessels in Laparoscopic Nephrectomy" Sales-Product Literature 2000.
Crouch et al. "A Velocity-Dependent Model for Needle Insertion in Soft Tissue" MICCAI 2005; LNCS 3750 pp. 624-632, dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales-Product Literature 1999.

\* cited by examiner

ELECTROSURGICAL INSTRUMENT WITH A KNIFE BLADE STOP

CROSS REFERENCE TO RELATED APPLICATION

The present application claims the benefit of and priority to U.S. Provisional Application Ser. No. 61/778,057, filed on Mar. 12, 2013, the entire contents of which are incorporated herein by reference.

BACKGROUND

Technical Field

The present disclosure relates to an electrosurgical instrument and, more particularly, to an electrosurgical instrument including a knife blade stop configured to limit distal movement of a knife blade of the electrosurgical instrument.

Description of Related Art

Electrosurgical forceps are well known in the medical arts. For example, an electrosurgical endoscopic forceps is utilized in surgical procedures, e.g., laparoscopic surgical procedure, where access to tissue is accomplished through a cannula or other suitable device positioned in an opening on a patient. The endoscopic forceps, typically, includes a housing, a handle assembly including a movable handle, a drive assembly, a shaft, a cutting mechanism such as, for example, a knife blade assembly, and an end effector assembly attached to a distal end of the shaft. The end effector includes jaw members that operably communicate with the drive assembly to manipulate tissue, e.g., grasp and seal tissue. Typically, the endoscopic forceps utilizes both mechanical clamping action and electrical energy to effect hemostasis by heating the tissue and blood vessels to coagulate, cauterize, seal, cut, desiccate, and/or fulgurate tissue. Typically, subsequent to effecting hemostasis, a knife blade of the knife blade assembly is deployed to sever the effected tissue.

Conventional endoscopic forceps, typically, utilize a safety blade lockout mechanism that prevents the blade from being unintentionally deployed. In particular, the endoscopic forceps may be configured to utilize a direct interaction between a lever and a trigger (or via another linkage in the lever mechanism) on the handle assembly to prevent the knife blade from being unintentionally deployed. That is, the knife blade is prevented from moving or translating into a knife slot on one or both of the jaw members. Under certain surgical scenarios, however, such as, for example, when the lever is in a "latched" configuration (i.e., the knife blade is operable to sever tissue) and a thick bundle of tissue is positioned between the jaw members, there exists a possibility of the knife blade deploying and wandering or drifting out of the knife slot(s) on the jaw member(s) and becoming trapped between the jaw members when they are moved to the clamping configuration. This condition is commonly referred to in the art as "blade trap." As can be appreciated, "blade trap" may cause a cutting edge of the knife blade to ineffectively sever electrosurgically treated tissue, i.e., the knife blade may not fully or "swiftly" sever the electrosurgically treated tissue.

SUMMARY

In view of the foregoing, it may prove useful in the medical arts to provide a knife blade stop configured limit distal movement of a knife blade of the electrosurgical instrument.

Aspects of the present disclosure are described in detail with reference to the drawing figures wherein like reference numerals identify similar or identical elements. As used herein, the term "distal" refers to the portion that is being described which is further from a user, while the term "proximal" refers to the portion that is being described which is closer to a user.

An aspect of the present disclosure provides an electrosurgical forceps with a shaft that extends from a housing of the electrosurgical forceps. An end effector assembly operably coupled to a distal end of the shaft includes a pair of first and second jaw members having proximal and distal ends. One or both of the first and second jaw members is movable from an open configuration for positioning tissue therebetween, to a clamping configuration for grasping tissue therebetween. A knife blade assembly includes a knife blade that is translatable within the first and second jaw members when the first and second jaw members are in the clamping configuration. The knife blade assembly includes a knife blade stop configured to contact at least a portion of the proximal end of the second jaw member when the first and second jaw members are in the open configuration to limit translation of the knife blade assembly.

The proximal ends of the first and second jaw members may be nested within each other. The proximal end of the second jaw member may be movably seated within the proximal of the first jaw member.

A leading edge of the second jaw member may be configured to contact a portion of the first jaw member when the first and second jaw members are in the open configuration. The first and second jaw members may each include one or more mechanical interfaces at the proximal end thereof. Moreover, the mechanical interfaces may be configured to contact one another when the first and second jaw members are in the clamping configuration. One of the mechanical interfaces may be one or more notched portions and the other one of the mechanical interfaces may be one or more corresponding protrusions.

An aspect of the present disclosure provides an electrosurgical forceps with a shaft that extends from a housing of the electrosurgical forceps. An end effector assembly is operably coupled to a distal end of the shaft and includes a pair of first and second jaw members having proximal and distal ends. The proximal end of the second jaw member is movable within the proximal end of the first jaw member to limit movement of the first and second jaw members between an open configuration for positioning tissue therebetween, to a clamping configuration for grasping tissue therebetween. A knife blade assembly includes a knife blade that is supported within the proximal ends of the first and second jaw members and is translatable within the first and second jaw members when the first and second jaw members are in the clamping configuration. The knife blade assembly includes a knife blade stop at a distal end thereof. The knife blade stop is configured to contact a portion of the proximal end of the second jaw member when the first and second jaw members are in the open configuration to limit translation of the knife blade assembly. The proximal end of the second jaw member is configured to contact a portion of the knife blade assembly to guide the knife blade into alignment with a knife channel provided on one (or both) of the first and second jaw members.

The proximal ends of the first and second jaw members may be nested with each other. The proximal end of the second jaw member may be movably seated within the proximal of the first jaw member.

A leading edge of the second jaw member may be configured to contact a portion of the first jaw member when the first and second jaw members are in the open configuration. The first and second jaw members may each include one or more mechanical interfaces at the proximal end thereof. Moreover, the mechanical interfaces may be configured to contact one another when the first and second jaw members are in the clamping configuration. One of the mechanical interfaces may be one or more notched portions and the other one of the mechanical interfaces may be one or more corresponding protrusions.

An aspect of the present disclosure provides an electrosurgical forceps with a shaft that extends from a housing of the electrosurgical forceps. An end effector assembly is operably coupled to a distal end of the shaft and includes a pair of first and second jaw members having proximal and distal ends. One or both of the first and second jaw members is movable from an open configuration for positioning tissue therebetween, to a clamping configuration for grasping tissue therebetween. A knife blade assembly includes a knife blade that is translatable within the first and second jaw members when the first and second jaw members are in the clamping configuration. The knife blade assembly includes a knife blade stop that includes a leading edge positioned to contact a trailing edge of a portion of the proximal end of the second jaw member when the first and second jaw members are in the open configuration to limit translation of the knife blade assembly. A leading edge of the second jaw member is configured to contact a leading edge of the first jaw member when the first and second jaw members are in the open configuration to limit pivoting of the first and second jaw members away from one another. The proximal end of the second jaw member is configured to contact a portion of the knife blade assembly to guide the knife blade into alignment with a knife channel provided on one (or both) of the first and second jaw members.

The proximal end of the second jaw member may be movably seated within the proximal of the first jaw member. The first and second jaw members may each include one or more mechanical interfaces at the proximal end thereof. Moreover, the mechanical interfaces may be configured to contact one another when the first and second jaw members are in the clamping configuration. One of the mechanical interfaces may be one or more notched portions and the other one of the mechanical interfaces may be one or more corresponding protrusions.

BRIEF DESCRIPTION OF THE DRAWING

Various embodiments of the present disclosure are described hereinbelow with references to the drawings, wherein.

DETAILED DESCRIPTION

Detailed embodiments of the present disclosure are disclosed herein; however, the disclosed embodiments are merely examples of the disclosure, which may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure.

The forceps of the instant disclosure includes a unique knife lock-out mechanism that is configured to prevent inadvertent advancement of a knife blade assembly of the forceps. Specifically, a proximal end of one of a pair of jaw members of the forceps is configured to contact a knife stop on the knife blade assembly when the jaw members are in an open configuration. This proximal end may further be configured to guide the blade assembly into alignment with knife channels provided on the jaw members. Moreover, the proximal ends of the jaw members are configured to limit how far the jaw members may pivot away from and toward one another.

Figure 1:
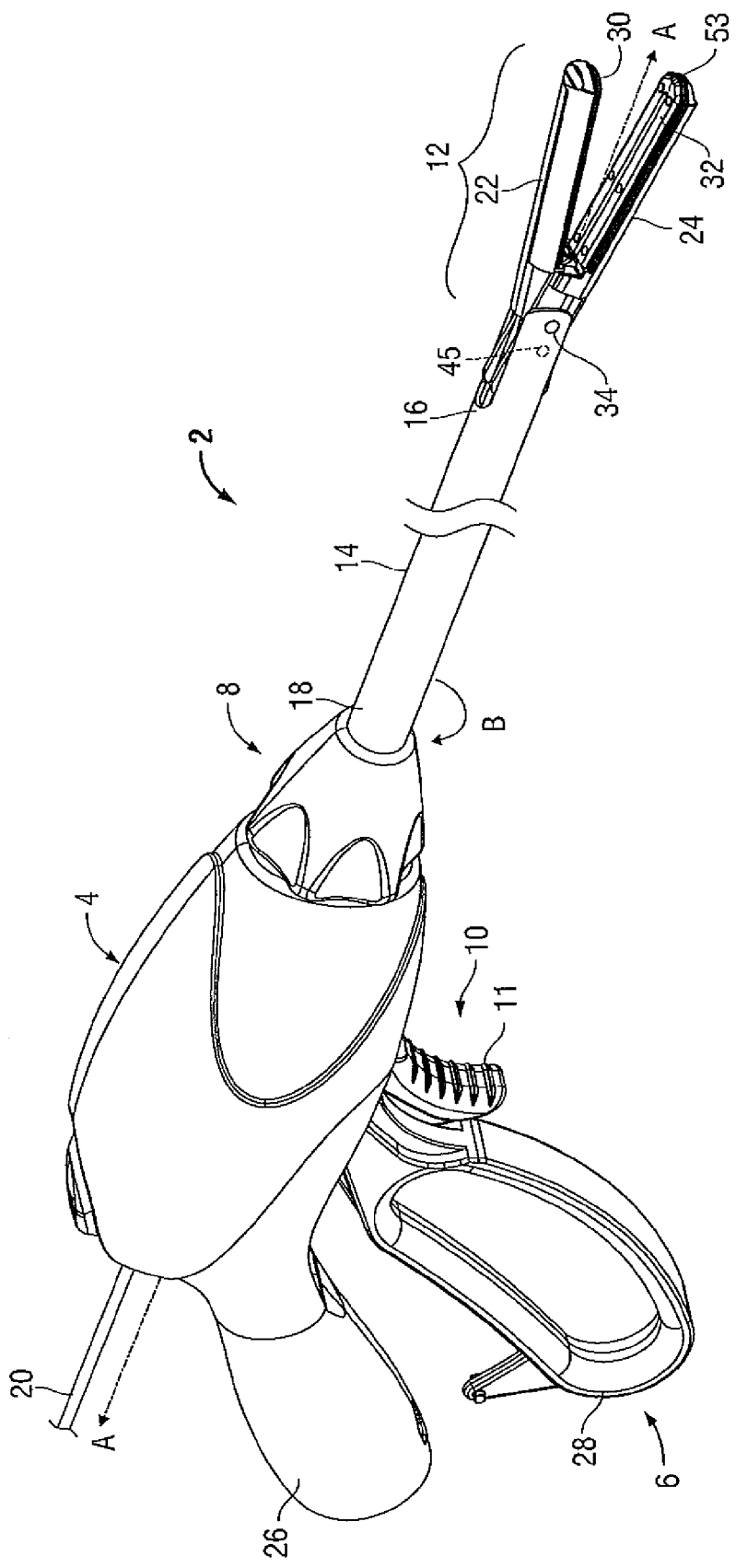
FIG. 1 is a perspective view of an endoscopic electrosurgical forceps according to an embodiment of the present disclosure.

Turning now to FIG. 1, an electrosurgical endoscopic forceps 2 (forceps 2) configured for use with a knife blade stop 40 (FIGS. 5-8) is illustrated. Forceps 2 includes a housing 4, a handle assembly 6, a rotating assembly 8, a trigger assembly 10 and an end effector assembly 12. Forceps 2 includes a shaft 14 that extends from housing 4 and has a longitudinal axis "A-A" defined therethrough. A distal end 16 of shaft 14 is configured to mechanically engage end effector assembly 12 and a proximal end 18 is configured to mechanically engage housing 4. Forceps 2 also includes an electrosurgical cable 20 that connects forceps 2 to a generator (not shown) or other suitable power source. Forceps 2 may alternatively be configured as a battery-powered instrument. Cable 20 includes a wire (or wires) (not explicitly shown) extending therethrough that has sufficient length to extend through shaft 14 in order to provide one or more suitable types of energy to one or both of a pair of jaw members 22 and 24 of end effector assembly 12. The generator may be configured to provide electrosurgical energy (e.g., RF, microwave, optical, etc.), thermal energy, ultrasonic energy, and the like to jaw members 22 and 24. In the illustrated embodiment, the generator is configured to provide RF energy to jaw members 22 and 24.

Rotating assembly 8 is rotatable in either direction about longitudinal axis "A-A" to rotate end effector 12 about longitudinal axis "A-A" (FIG. 1). Housing 4 houses the internal working components of forceps 2, such as a drive assembly (not explicitly shown), working components of handle assembly 6, electrical raceways associated with cable 20, and other working components therein.

Figure 6:
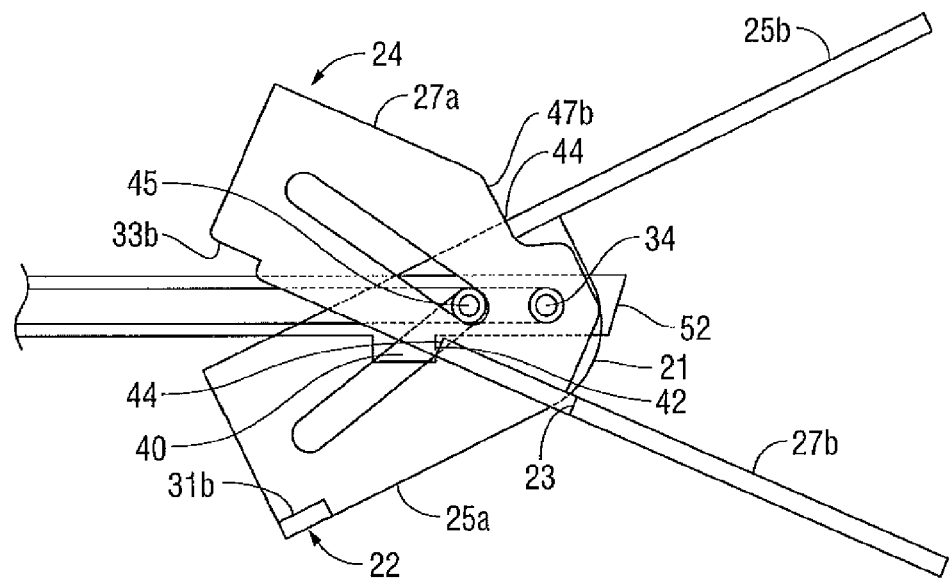
FIG. 6 is a side, schematic, perspective view of the jaw members depicted in an open configuration and the knife blade assembly in a retracted configuration.

Handle assembly 6 includes a fixed handle 26 and a moveable handle 28. Fixed handle 26 is integrally associated with housing 4 and movable handle 28 is moveable relative to fixed handle 26. Moveable handle 28 connects to the drive assembly such that, together, movable handle 28 and the drive assembly mechanically cooperate to impart movement of jaw members 22 and 24 between a spaced-apart position and an approximated position to grasp tissue disposed between treatment surfaces 30 and 32 of jaw members 22, 24, respectively. As shown in FIG. 1, moveable handle 28 is initially spaced-apart from fixed handle 26 and, correspondingly, jaw members 22, 24 are in the spaced-apart position (FIGS. 1 and 6). Moveable handle 28 is depressible from this initial position (FIG. 1) to a depressed position (not explicitly shown) corresponding to the approximated position of jaw members 22, 24.

Other methods for opening and closing the jaw members 22, 24 may be utilized. For example, any number of linkage devices, gears, vacuum tubes, actuators and the like may be utilized alone or in combination with the movable handle 24 and/or drive assembly to impart movement of the jaw members 22, 24 from the spaced-apart position to the approximated position.

Figure 2:
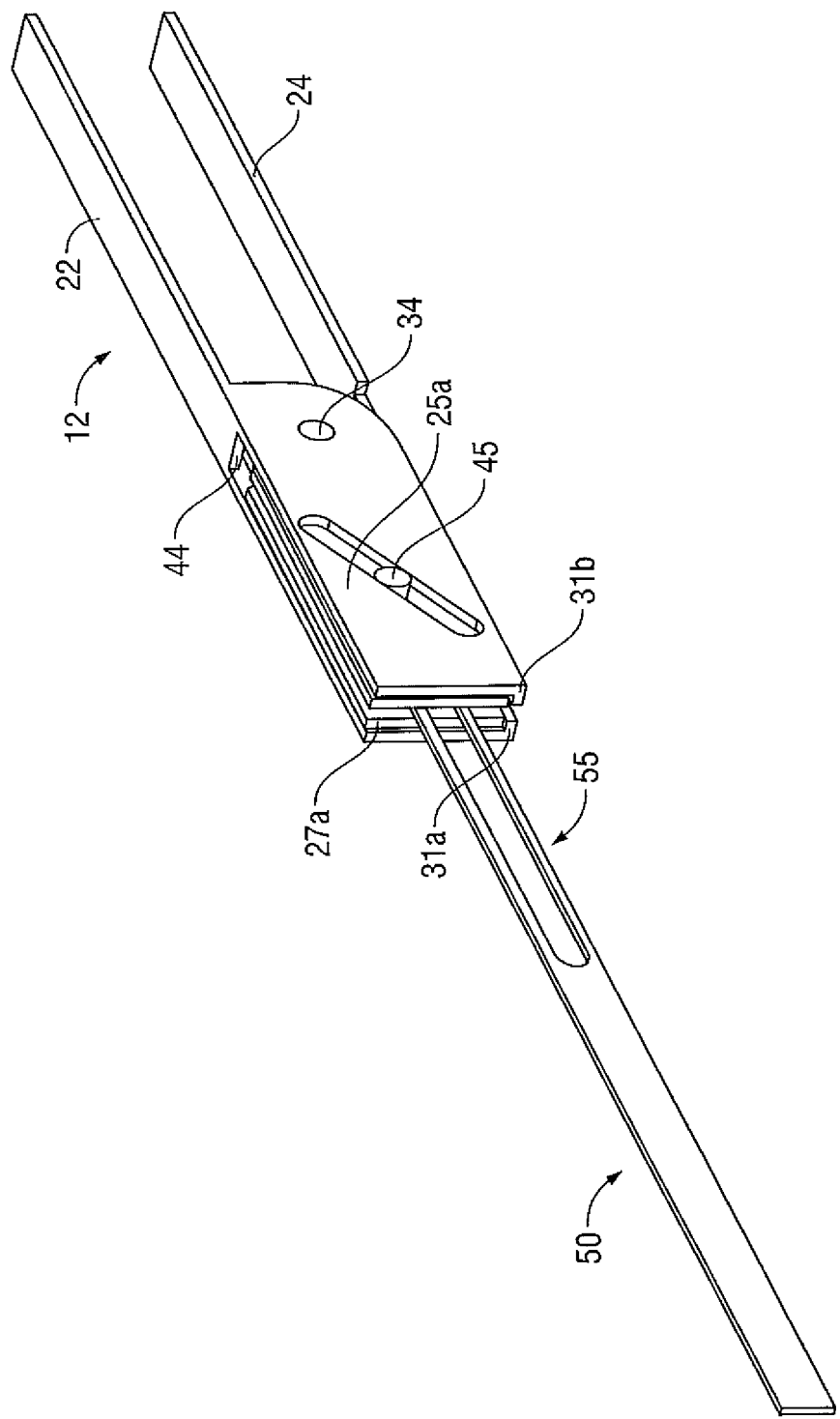
FIG. 2 is a schematic, perspective view of jaw members coupled to a knife blade assembly configured for use with the endoscopic forceps depicted in FIG. 1.

Continuing with reference to FIGS. 1-2, end effector assembly 12 is designed as a bilateral assembly, i.e., where both jaw member 22 and jaw member 24 are moveable about pivot pin 34 relative to one another and to shaft 14. End effector assembly 12, however, may alternatively be configured as a unilateral assembly, i.e., where jaw member 24 is fixed relative to shaft 14 and jaw member 22 is moveable about pivot 34 relative to shaft 14 and fixed jaw member 24.

Figure 3:
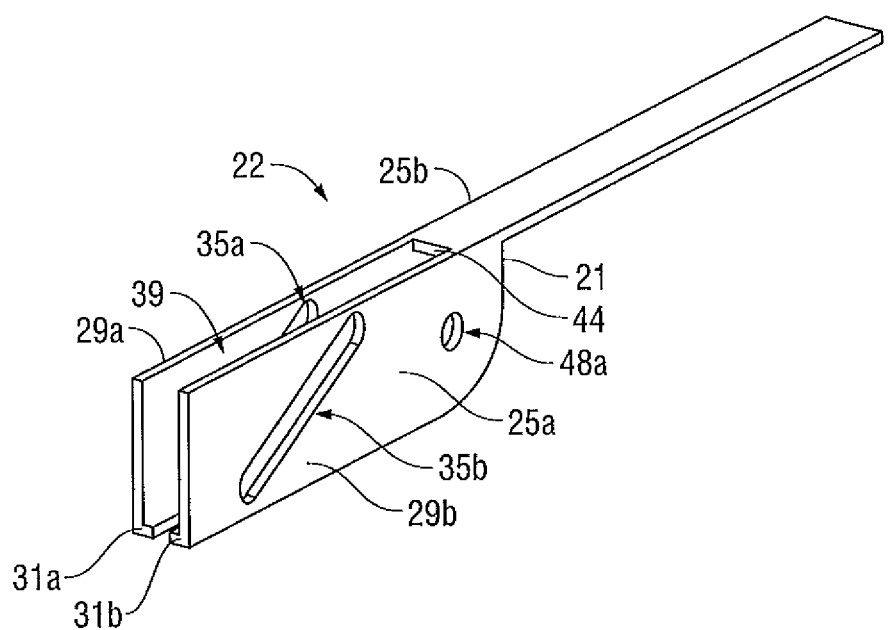
FIG. 3 is a schematic, perspective view of a top jaw member depicted in FIG. 2.

Referring to FIG. 3, jaw member 22 includes a proximal end 25a and a distal end 25b of suitable configuration that is configured to support treatment surface 30 thereon. Proximal end 25a includes a bifurcated configuration defined by left and right sidewalls 29a, 29b having a suitable configuration to receive a proximal end 27a of jaw member 24 (see FIG. 2 for example). Cam slots 35a, 35b are provided on sidewalls 29a, 29h and are configured to receive a cam pin 45 (FIGS. 1-2) that is operably coupled to the drive assembly and is configured to impart movement of jaw members 22, 24 when movable handle 28 is moved proximally. Moreover, apertures 48a are defined through sidewalls 29a, 29h and are configured to receive pivot pin 34 therein to allow jaw members 22, 24 to pivot thereabout when jaw members 22, 24 are moved from the open configuration to the clamping configuration (and vice versa).

Continuing with reference to FIG. 3, one or more mechanical interfaces are provided on proximal end 25a and are configured to contact one or more corresponding mechanical interfaces provided on proximal end 27a of jaw member 24 when jaw members 22, 24 are in the clamping configuration. In the illustrated embodiment, for example, the mechanical interface provided on proximal end 25a is in the form of a pair of protrusions 31a, 31b that extend inwardly from a bottom surface of respective sidewalls 29a, 29b. Protrusions 31a, 31b are configured to selectively engage a pair of corresponding notches 33a, 33b (FIGS. 4A-4B) provided on jaw member 24 to ensure a specific gap distance is maintained between jaw members 22, 24 when jaw members 22, 24 are in the clamping configuration (see FIGS. 2 and 7 for example).

A leading edge 44 (FIGS. 2-3) is provided on proximal end 25a and is configured to selectively contact a pair of corresponding leading edges 47a, 47b on proximal end 27a (FIGS. 4A-4B) when jaw members 22, 24 are moved to the open configuration. Contact between leading edge 44 and leading edges 47a, 47b prevents a user from opening jaw members 22, 24 too far apart from one another (see FIG. 6 for example).

Figure 4A:
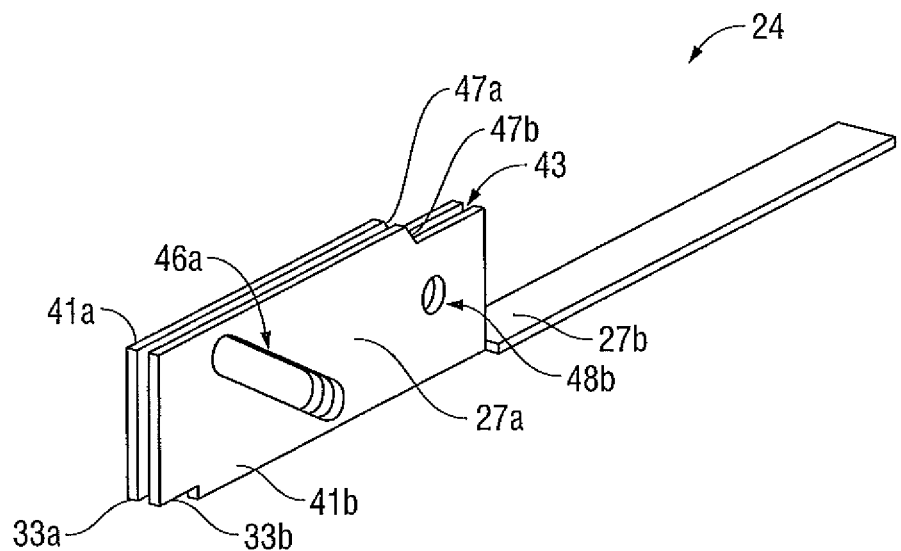
FIGS. 4A and 4B are schematic, perspective views of a bottom jaw member depicted in FIG. 2 shown from respective top and bottom elevational perspectives.
Figure 4B:
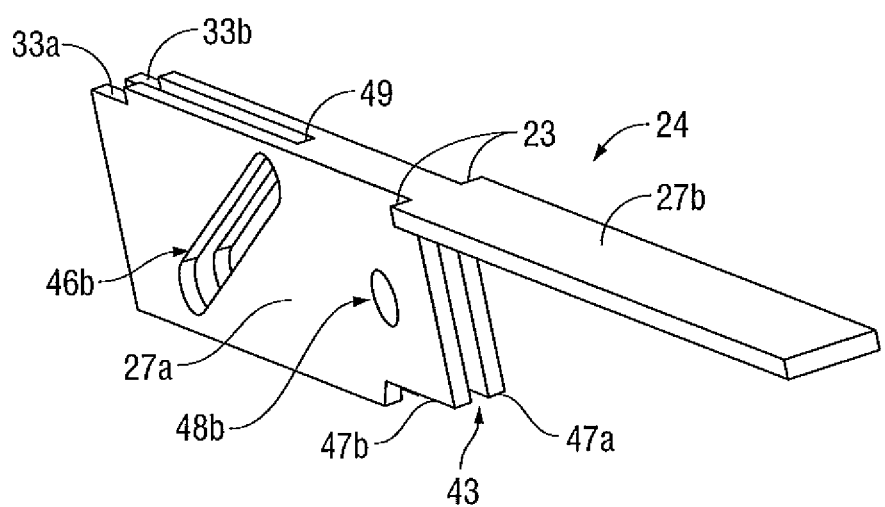

Referring to FIGS. 4A-4B, jaw member 24 includes proximal end 27a and a distal end 27b of suitable configuration that is configured to support treatment surface 32 thereon. Proximal end 27a includes a bifurcated configuration defined by left and right sidewalls 41a, 41b. Sidewalls 41a, 41b define a cavity 43 of suitable configuration that is configured to receive a knife blade assembly 50 (FIG. 2) therethrough. Cam slots 46a, 46b are provided on sidewalls 41a, 41b and are configured to receive cam pin 45 that functions to impart movement of jaw member 24 in a manner as described above. Apertures 48b are defined through sidewalls 41a, 41b and are configured to receive pivot pin 34 therein. As noted above, leading edges 47a, 47b are configured to contact leading edge 44 and notches 33a, 33b are configured to contact protrusions 31a, 31b. A trailing edge 49 (FIG. 4B) is provided on jaw member 24 and is configured to selectively engage a knife blade assembly 50 to prevent distal translation of knife blade 52, as will be described below. In embodiments, a pair of trailing edges 23 of the distal end 27b may be configured to contact a proximal face 21 of the proximal end 25a of the jaw member 22 to prevent a user from opening jaw members 22, 24 too far apart from one another (see FIG. 6 for example).

In an assembled configuration proximal ends 25a, 27a of jaw members 22, 24, respectively, are nested with each other such that proximal end 27a of jaw member 24 is movably seated within proximal end 25a of jaw member 22 so as to allow jaw members 22, 24 to move between the open and clamping configurations (as best seen in FIG. 2). Moreover, knife blade channels 53 (one knife channel shown in FIG. 1) are provided on jaw members 22, 24 and are aligned with the knife blade assembly 50 to accommodate reciprocation of a knife blade 52 through jaw members 22, 24 when a trigger 11 of the trigger assembly 10 is moved proximally (FIGS. 1 and 2) and jaw members 22, 24 are in the clamping configuration.

Figure 5:
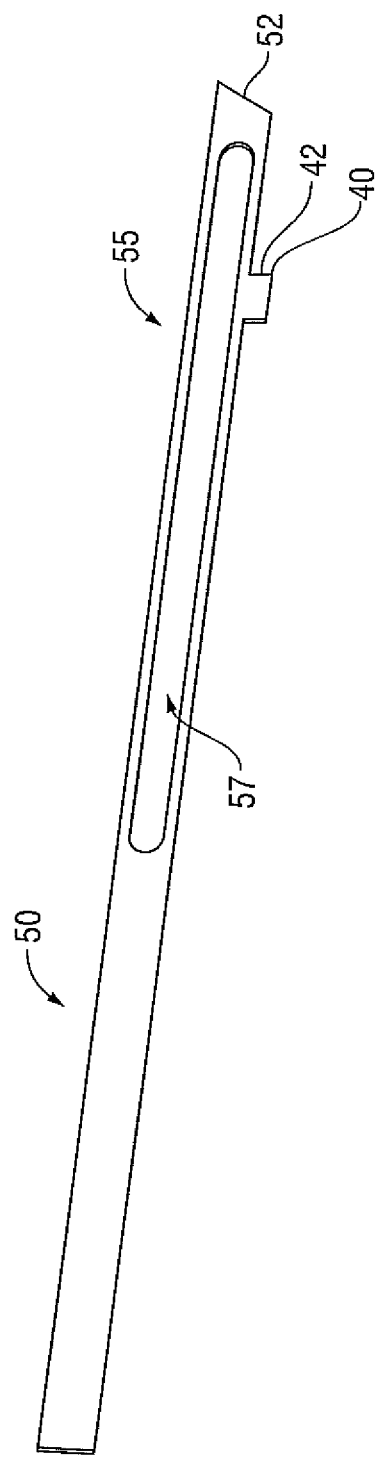
FIG. 5 is a perspective view of the knife blade assembly depicted in FIG. 2.

Referring now to FIG. 5, knife blade assembly 50 is disposed within shaft 14 and is translatable therethrough from an initial, retracted configuration to an extended configuration into knife blade channels 53 on the jaw members 22, 24. Knife blade assembly 50 includes a generally elongated configuration having a split or bifurcated medial portion 55 defining opening 57 therebetween that is configured to receive pivot pin 34 and cam pin 45 therethrough (FIG. 2).

A knife blade stop 40 (FIG. 5) is provided on knife blade assembly 50 and is positioned proximally with respect to knife blade 52 to selectively contact a portion of jaw member 24. Specifically, knife blade stop 40 is provided at a bottom portion of knife blade assembly 50 and includes a generally rectangular configuration having a leading edge 42 that is configured to contact trailing edge 49 of proximal end 27a of jaw member 24.

Figure 9:
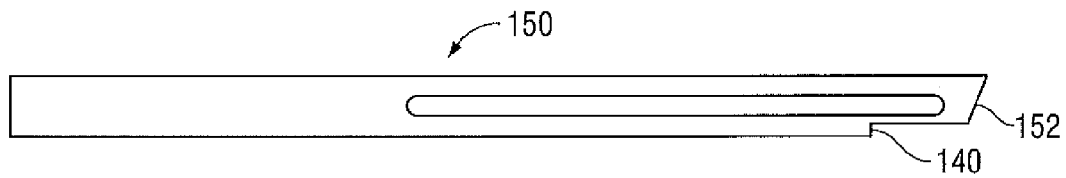
FIG. 9 is side view of a knife blade assembly configured for use with the endoscopic forceps depicted in FIG. 1 according to another embodiment.

In embodiments (see FIG. 9 for example), a knife blade assembly 150 may include a knife blade stop 140 that includes a leading edge 142. Unlike the knife blade stop 40 of the knife blade assembly 50, the knife blade stop 140 extends substantially along a length of a bottom portion of the knife blade assembly 150 which provides a knife blade assembly 150 that is taller than known knife blade assemblies that are configured for use with conventional forceps.

In embodiments, it may prove useful to provide knife blade assemblies 50, 150 including respective knife blade stops 40, 140 that are thicker than conventional knife blade assemblies. As can be appreciated, the knife blade assemblies 50, 150 may include a thickness that serves to strengthen the knife blades 52, 152 which may reduce breakage thereof when the knife blade assemblies 50, 150 are moved to advance the knife blades 52, 152 distally through the jaw members 22, 24 to sever tissue.

The thickness of the knife blade assemblies 50, 150 and/or the knife stops 40, 140 may be adjusted to achieve various effects and/or end results. For example, thicker knife blade assemblies 50, 150 including the knife blade stops 40, 140 may be utilized to facilitate guiding the knife blades 52, 152 into alignment with the knife channels 53 on the jaw members 22, 24 without the need for any additional part(s). That is, the thicker knife blade assemblies 50, 150 including the knife blade stops 40, 140 may be effectively "pinched" between the left and right sidewalls 41a, 41b of the proximal end 27a of jaw member 24 as the knife blades 52, 152 are advanced through the knife channel 53 on the jaw members 22, 24.

In use, jaw members 22, 24, initially, may be in the open configuration (FIG. 6) so that a user may position tissue between jaw members 22, 24. In the open configuration, leading edge 42 of blade stop 40 contacts trailing edge 49 of jaw member 24, which prevents distal translation of knife blade assembly 50 including knife blade 52 through jaw members 22, 24 (FIG. 6). Moreover, jaw members 22, 24 are prevented from excessively pivoting (or opening) away from one another when large tissue is positioned therebetween. Specifically, contact between edges 47a, 47b and edge 44 prevents jaw members 22, 24 from excessively pivoting away from one another.

Figure 7:
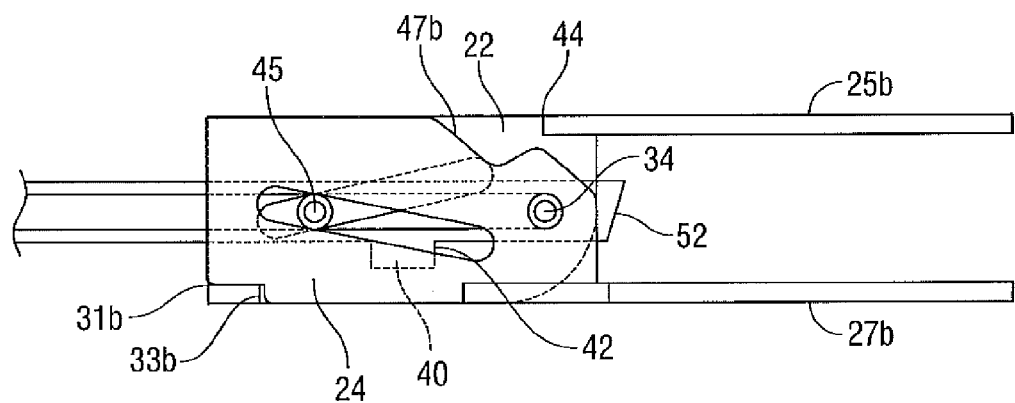
FIG. 7 is a side, schematic, perspective view of the jaw members depicted in a closed configuration and the knife blade assembly in a retracted configuration.
Figure 8:
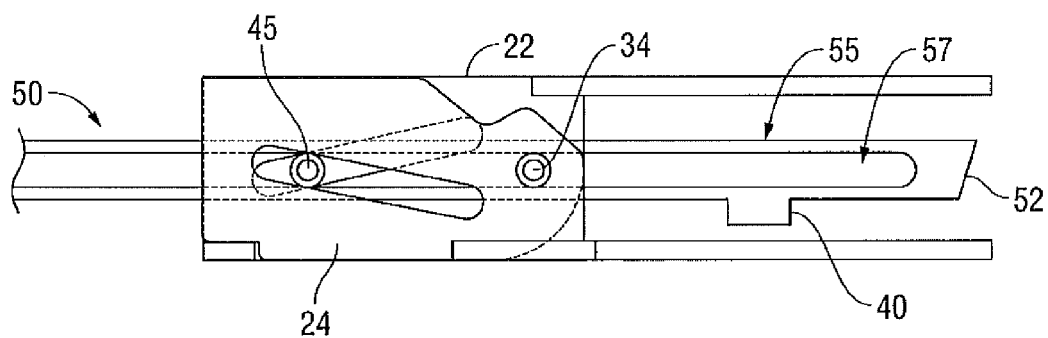
FIG. 8 is a side, schematic, perspective view of the jaw members depicted in a closed configuration and the knife blade assembly in an extended configuration.

Thereafter, movable handle 28 may be moved proximally to move jaw members 22, 24 to a clamping configuration (FIG. 7). In the clamping configuration, a predetermined gap distance (e.g., 0.001 inches to about 0.006 inches) is maintained between jaw members 22, 24 as a result of notches 33a, 33b contacting protrusions 31a, 31b; this also offloads some of the closure forces against cam pin 45. In the clamping configuration, trailing edge 49 is rotated out of a path of translation of knife blade 52 and out of contact with leading edge 42 so as to allow advancement of the knife blade assembly 50 including knife blade 52. Subsequently, trigger 11 of trigger assembly 10 may be actuated to move the knife blade assembly 50 including the knife blade 40 distally to advance the knife blade 52 through the knife channel 53 on the jaw members 22, 24 to sever tissue (FIG. 8). The left and right sidewalls 41a, 41b of the proximal end 27a of jaw member 24 help guide the knife blade 52 into alignment with the knife channels 53 on the jaw members 22, 24.

The unique configuration of the blade stop 40 overcomes the aforementioned drawbacks that are typically associated with conventional forceps that utilize one or more components associated therewith to limit proximal and/or distal movement of the knife blade assembly. In particular, the likelihood of the knife blade assembly 50 including the knife blade 52 inadvertently moving between the jaw members 22, 24, such as, for example, when large tissue is positioned therebetween, is greatly reduced, if not completely eliminated. In other words, this greatly reduces, if not completely eliminates "blade trap" from occurring.

Moreover, providing jaw member 24 with notches 33a, 33b that are configured to contact corresponding protrusions 31a, 31b on jaw member 22 ensures that a specific gap distance is maintained between the jaw members 22, 24 when the jaw members 22, 24 are in the clamping configuration. As can be appreciated, this may prove advantageous during surgical procedures that require a specific gap distance between the jaw members when the jaw members are electrosurgically treating tissue, e.g., sealing tissue. Further, the overall manufacturing costs of the forceps 10 is kept relatively low as a result of being able to utilize the proximal end 27a of jaw member 24 to help guide the knife blade 52 into alignment with the knife channels 53.

From the foregoing and with reference to the various figure drawings, those skilled in the art will appreciate that certain modifications can also be made to the present disclosure without departing from the scope of the same. For example, in certain instances one or more resilient members, such as, for example, a spring or the like may be operably coupled to blade stop 40 to facilitate returning the knife blade assembly back to the retracted position.

Figure 10:
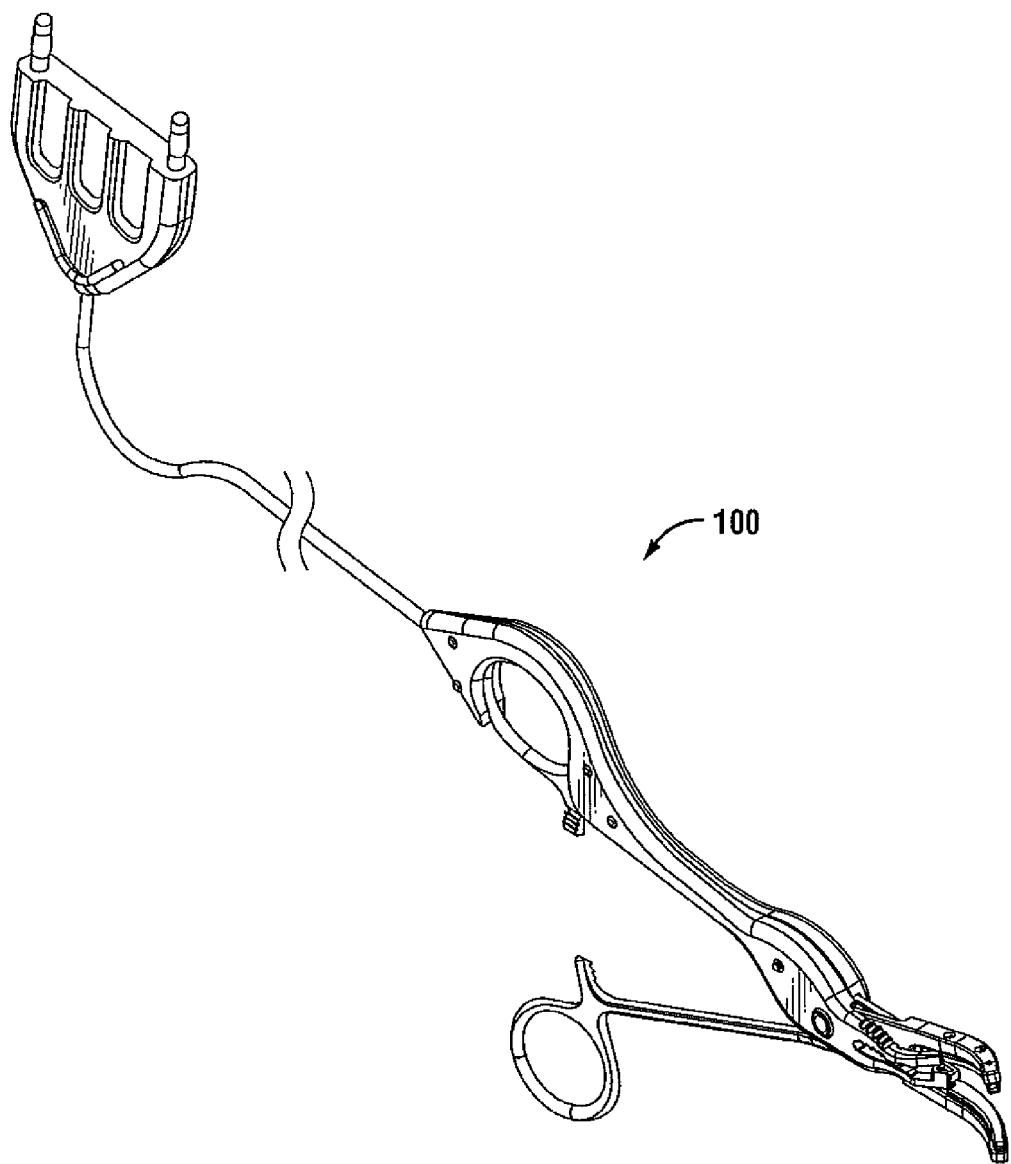
FIG. 10 is a perspective view of an open electrosurgical forceps configured for use with a knife blade assembly according to an embodiment of the present disclosure.

While blade stop 40 has been described in terms of use with an endoscopic forceps, it is within the purview of the present disclosure that blade stop 40 may be configured for use with an open forceps 100, see FIG. 10 for example. In this instance, blade stop 40 may be configured to accommodate the specific design of the open forceps.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An electrosurgical forceps, comprising:
    a housing having a shaft extending therefrom;
    an end effector assembly operably coupled to a distal end of the shaft and including a pair of first and second jaw members having proximal and distal ends, at least one of the first or second jaw members movable from an open configuration for positioning tissue therebetween, to a clamping configuration for grasping tissue therebetween, the proximal end of the first jaw member defining a central longitudinal axis and including a left sidewall disposed on a first side of the central longitudinal axis and a right sidewall disposed on a second side of the central longitudinal axis, the proximal end of the first jaw member defining a cavity between the left and right sidewalls, the cavity configured for receipt of the proximal end of the second jaw member; and
    a knife blade assembly including:
        a knife blade translatable within the first and second jaw members when the first and second jaw members are in the clamping configuration; and
        a knife blade stop protruding laterally from the knife blade and having a distally-oriented edge terminating proximally of a distal cutting edge of the knife blade, the distally-oriented edge of the knife blade stop configured to contact at least a portion of the proximal end of the second jaw member when the first and second jaw members are in the open configuration to limit distal translation of the knife blade assembly.

2. An electrosurgical forceps according to claim 1, wherein the proximal end of the second jaw member includes a planar, left sidewall and a planar, right sidewall each configured to be nested within the cavity of the proximal end of the first jaw member such that the proximal end of the second jaw member is movably seated within the cavity of the proximal end of the first jaw member.

3. An electrosurgical forceps according to claim 1, wherein a leading edge of the second jaw member is configured to contact a leading edge of the first jaw member when the first and second jaw members are in the open configuration.

4. An electrosurgical forceps according to claim 1, wherein the first and second jaw members each include at least one mechanical interface at the proximal end thereof that are configured to contact one another when the first and second jaw members are in the clamping configuration.

5. An electrosurgical forceps according to claim 4, wherein one of the mechanical interfaces is at least one notched portion and the other of the mechanical interfaces is a corresponding protrusion extending inwardly from the first sidewall of the proximal end of the first jaw member into the cavity of the proximal end of the first jaw member.

6. The electrosurgical forceps according to claim 1, wherein the left and right sidewalls are spaced from one another along a horizontal axis that is substantially perpendicular relative to the central longitudinal axis of the proximal end of the first jaw member.

7. An electrosurgical forceps, comprising:
a housing having a shaft extending therefrom;
an end effector assembly operably coupled to a distal end of the shaft and including a pair of first and second jaw members having proximal and distal ends, the proximal end of the second jaw member movable within the proximal end of the first jaw member to limit movement of the first and second jaw members between an open configuration for positioning tissue therebetween, to a clamping configuration for grasping tissue therebetween, the proximal end of the first jaw member including a planar, left sidewall and a planar, right sidewall and defining a rectangular-shaped cavity therebetween configured for receipt of the proximal end of the second jaw member; and
a knife blade assembly including:
a knife blade supported within the proximal ends of the first and second jaw members and translatable within the first and second jaw members when the first and second jaw members are in the clamping configuration; and
a knife blade stop protruding laterally from a distal end of the knife blade and having a distally-oriented edge terminating proximally of a distal cutting edge of the knife blade, the knife blade stop configured to contact at least a portion of the proximal end of the second jaw member when the first and second jaw members are in the open configuration to limit translation of the knife blade assembly,
wherein the proximal end of the second jaw member is configured to contact at least a portion of the knife blade assembly to guide the knife blade into alignment with a knife channel provided on at least one of the first and second jaw members.

8. An electrosurgical forceps according to claim 7, wherein the proximal end of the second jaw member includes an elongated left sidewall and an elongated right sidewall each configured to be nested within the cavity of the proximal end of the first jaw member such that the proximal end of the second jaw member is movably seated within the cavity of the proximal end of the first jaw member.

9. An electrosurgical forceps according to claim 7, wherein a leading edge of the second jaw member is configured to contact a leading edge of the first jaw member when the first and second jaw members are in the open configuration.

10. An electrosurgical forceps according to claim 7, wherein the first and second jaw members each include at least one mechanical interface at the proximal end thereof that are configured to contact one another when the first and second jaw members are in the clamping configuration.

11. An electrosurgical forceps according to claim 10, wherein one of the mechanical interfaces is at least one notched portion and the other of the mechanical interfaces is a corresponding protrusion extending inwardly from the first sidewall of the proximal end of the first jaw member into the cavity of the proximal end of the first jaw member.

12. An electrosurgical forceps, comprising:
a housing having a shaft extending therefrom;
an end effector assembly operably coupled to a distal end of the shaft and including a pair of first and second jaw members having proximal and distal ends, at least one of the first and or second jaw members movable from an open configuration for positioning tissue therebetween, to a clamping configuration for grasping tissue therebetween, the proximal end of the first jaw member defining a central longitudinal axis and including a left sidewall and a right sidewall and defining a cavity therebetween configured for receipt of the proximal end of the second jaw member, each of the left and right sidewalls defining a longitudinal axis that is substantially parallel with the central longitudinal axis of the proximal end of the first jaw member; and
a knife blade assembly including:
a knife blade translatable within the first and second jaw members when the first and second jaw members are in the clamping configuration, the knife blade including a distal cutting edge; and
a knife blade stop protruding laterally from the knife blade and defining a leading edge positioned to contact a trailing edge of at least a portion of the proximal end of the second jaw member when the first and second jaw members are in the open configuration to limit translation of the knife blade assembly, the leading edge of the knife blade stop terminating proximally of the distal cutting edge of the knife blade,
wherein a leading edge of the second jaw member is configured to contact a leading edge of the first jaw member when the first and second jaw members are in the open configuration to limit pivoting of the first and second jaw members away from one another,
wherein the proximal end of the second jaw member is configured to contact at least a portion of the knife blade assembly to guide the knife blade into alignment with a knife channel provided on at least one of the first and second jaw members.

13. An electrosurgical forceps according to claim 12, wherein the proximal end of the second jaw member includes a left sidewall and a right sidewall movably seated within the cavity of the proximal end of the first jaw member.

14. An electrosurgical forceps according to claim 12, wherein the first and second jaw members each include a mechanical interface at the proximal end thereof, the mechanical interfaces configured to contact one another when the first and second jaw members are in the clamping configuration, wherein one of the mechanical interfaces is a notched portion and the other mechanical interface is a corresponding protrusion extending inwardly from the first sidewall of the proximal end of the first jaw member into the cavity of the proximal end of the first jaw member.

15. The electrosurgical forceps according to claim 12, wherein the left and right sidewalls are spaced from one another along a horizontal axis that is substantially perpendicular relative to the central longitudinal axis of the proximal end of the first jaw member.

* * * * *